(12) United States Patent
Kabilan et al.

(10) Patent No.: US 7,998,639 B2
(45) Date of Patent: Aug. 16, 2011

(54) HOLOGRAPHIC SENSOR

(75) Inventors: Satyamoorthy Kabilan, Cambridge (GB); Alexander James Marshall, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 848 days.

(21) Appl. No.: 11/662,114

(22) PCT Filed: Sep. 7, 2005

(86) PCT No.: PCT/GB2005/003446
§ 371 (c)(1),
(2), (4) Date: May 16, 2007

(87) PCT Pub. No.: WO2006/027575
PCT Pub. Date: Mar. 16, 2006

(65) Prior Publication Data
US 2008/0068684 A1    Mar. 20, 2008

(30) Foreign Application Priority Data

Sep. 7, 2004  (GB) .................................. 0419827.1

(51) Int. Cl.
*G03H 1/04*   (2006.01)
*G01N 21/47*  (2006.01)
(52) U.S. Cl. .................................... 430/2; 430/1; 359/3
(58) Field of Classification Search .................. None
See application file for complete search history.

(56) References Cited

U.S. PATENT DOCUMENTS

| | | | | |
|---|---|---|---|---|
| 4,563,024 A | * | 1/1986 | Blyth | ............................. 283/91 |
| 5,795,681 A | | 8/1998 | Muller et al. | |
| 5,857,709 A | | 1/1999 | Chock | |
| 5,989,923 A | * | 11/1999 | Lowe et al. | .................... 436/518 |
| 6,066,378 A | * | 5/2000 | Morii et al. | .................. 428/40.2 |
| 6,689,316 B1 | * | 2/2004 | Blyth et al. | ..................... 422/56 |
| 7,443,553 B2 | * | 10/2008 | Lowe et al. | ....................... 359/9 |
| 2004/0106075 A1 | * | 6/2004 | Cuong et al. | .................. 430/449 |
| 2006/0234132 A1 | * | 10/2006 | Davidson et al. | ................. 430/1 |
| 2007/0285746 A1 | * | 12/2007 | Millington et al. | ............... 359/2 |
| 2009/0207465 A1 | * | 8/2009 | Riddle et al. | ...................... 359/2 |
| 2009/0272805 A1 | * | 11/2009 | Riddle et al. | .................. 235/457 |

FOREIGN PATENT DOCUMENTS

| | | |
|---|---|---|
| DE | 100 26 620 A1 | 3/2002 |
| EP | 0 345 405 | 12/1989 |
| WO | WO 99/63408 | 12/1999 |
| WO | 01/50113 * | 7/2001 |
| WO | 2004/081676 * | 9/2004 |
| WO | WO 2004/081546 | 9/2004 |
| WO | WO 2005/031442 | 4/2005 |

OTHER PUBLICATIONS

Kabilan et al. "Glucose-sensitive holographic sensors" J. Mol. Recognit., vol. 17 pp. 162-166 (2004, on-line Apr. 27, 2004).*
Lowe et al., "Holograms that react to biological substances offer new diagnostic tools", oemagazine (6 pages (Mar. 2003).*
Mayes et al, "Aholographic alcohol sensor", Anal. Chem., vol. 71 pp. 3390-3396 (Aug. 1999).*
Kim et al., "Holographic optical elements recorded in silver halide sensitized gelatin emulsions. Part 1. Transmission holographic optical elements," *Applied Optics*, Feb. 10, 2001, vol. 40, No. 5, pp. 622-632.
Hochstrasser et al., "Development of Polyacrylamide Gels that Improve the Separation of Proteins and Their Detection by Silver Staining," *Analytical Biochemistry*, 1988, vol. 173, pp. 412-423.

* cited by examiner

*Primary Examiner* — Martin J Angebranndt
(74) *Attorney, Agent, or Firm* — Saliwanchik, Lloyd & Eisenchenk

(57) ABSTRACT

The invention relates to a sensor comprising a medium and, disposed therein, a hologram, wherein an optical characteristic of the medium changes as a result of a variation in a physical property of the medium, wherein the fringes of the hologram are formed by silver grains and wherein the medium comprises a material which does not bind silver. The brightness and sensitivity of such holographic sensors is increased as a result of reduction in the levels of unwanted ("background") silver binding.

19 Claims, No Drawings

HOLOGRAPHIC SENSOR

This application is a National Stage Application of International Application Number PCT/GB2005/003446, filed Sep. 7, 2005; which claims priority to Great Britain Application No. 0419827.1, filed Sep. 7, 2004.

FIELD OF THE INVENTION

This invention relates to a holographic sensor.

BACKGROUND TO THE INVENTION

WO-A-95/26499 describes a holographic sensor. The sensor comprises a holographic support medium and, disposed throughout its volume, a hologram. The support medium interacts with an analyte, resulting in a variation of a physical property of the medium. This variation induces a change in an optical characteristic of the holographic element, such as its polarisability, reflectance, refractance or absorbance. If any change occurs whilst the hologram is being replayed (e.g. using incident broad band, non-ionising electromagnetic radiation), then a colour change, for example, may be observed using an optical detector. The optical detector may be a spectrometer or simply the human eye.

WO-A-99/63408 describes an alternative method of producing a holographic sensor. A sequential treatment technique is used, wherein the polymer film is made first and sensitive silver halide particles are incorporated subsequently. These particles are introduced by diffusing soluble salts into the polymer matrix and reacting them with halide ions and a sensitising dye, to form an insoluble light-sensitive precipitate. The holographic image is then recorded.

PCT/GB04/00976 describes how holographic sensors can be produced using a technique known as "silverless double polymerisation".

Holographic sensors have been proposed for subcutaneous use, e.g. to detect glucose. However, the holograms do not generally reflect light of sufficient intensity to penetrate through the skin and be detected. This is mainly because of problems of light scatter.

The support medium of a conventional holographic sensor may comprise a cross-linker such as N,N'-methylenebisacrylamide (MBA).

Hochstrasser et al, Analytical Biochemistry (1988) Volume 173, pages 412-423, report investigating several different cross-linkers in acrylamide gels, to limit the background binding of silver to the gel when carrying out silver staining of the gel. They found that any cross-linker with free amides such a methylenebisacrylamide (MBA) tended to cause a lot of background staining. They postulated that the free amides on MBA were responsible for interacting with the silver and binding it to the polymer. They found that bisacryloylpiperazine (BAP) which is a tertiary amide (unlike MBA and most other bisacrylamide cross-linkers, which are secondary amides) did not exhibit this random binding and high silver background during silver staining. This was thought to be due to the nitrogens in BAP being unable to interact with silver.

SUMMARY OF THE INVENTION

The present invention is based on a realisation that the brightness and sensitivity of holographic sensors can be increased by reducing the levels of unwanted ("background") silver binding.

According to a first aspect of the invention, a sensor comprises a medium and, disposed therein, a hologram, wherein an optical characteristic of the medium changes as a result of a variation in a physical property of the medium, wherein the fringes of the hologram are formed by silver grains and wherein the medium comprises a material which inhibits the binding of unwanted silver. Preferably, the medium is an acrylamide-based material cross-linked with a bis(tertiary amide) such as 1,4-bis(acryloyl)piperazine.

A second aspect of the invention is a subcutaneous implant, which comprises a sensor of the invention.

Sensors of the invention may be substantially brighter and more sensitive than conventional sensors, and the light which they reflect may be highly monochromatic, having a greater resolution. It follows that sensors of the invention are particularly suitable for use subcutaneously, e.g. in the detection of glucose or lactic acid. The sensors may also be used in security/authentication.

DESCRIPTION OF PREFERRED EMBODIMENTS

In a preferred embodiment of the invention, and for the purpose of illustration, the holographic support medium is a material cross-linked with 1,4-bis(acryloyl)piperazine (BAP), the structure of which is:

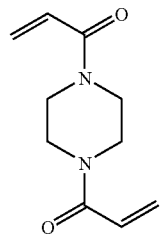

Without wishing to be bound by theory, it is believed that the presence of a cross-linking agent such as BAP inhibits the random (or non-specific) binding of silver to the support medium, thereby minimising the background noise which results from the holographic recording process.

A holographic sensor of the type used in the invention generally comprises a medium and, disposed throughout the volume of the medium, a hologram. The support medium may interact with an analyte resulting in a variation of a physical property of the medium. This variation induces a change in an optical characteristic of the holographic element, such as its polarisability, reflectance, refractance or absorbance. If any change occurs whilst the hologram is being replayed by incident broad band, non-ionising electromagnetic radiation, then a colour or intensity change, for example, may be observed.

There are a number of basic ways to change a physical property, and thus vary an optical characteristic. The physical property that varies is preferably the volume of the support medium and, in turn, the spacing of the holographic fringes of the holographic element. This variation may be achieved by incorporating specific groups into the support matrix, where these groups undergo a change in, for example, conformation, charge or the degree of cross-linking upon interaction with the analyte, and cause an expansion or contraction of the support medium. Such a group is preferably the specific binding conjugate of an analyte species.

A holographic sensor may be used for detection of a variety of analytes, simply by modifying the composition of the support medium. The medium preferably comprises a polymer matrix, the composition of which must be optimised to obtain a high quality film, i.e. a film having a uniform matrix in which holographic fringes can be formed. It is preferred that the medium is obtained by the (co)polymerisation of monomers including acrylamide-based monomers.

Other examples of holographic support media are gelatin, K-carageenan, agar, agarose, polyvinyl alcohol (PVA), sol-gels (as broadly classified), hydrogels (as broadly classified), and acrylates. Further materials are polysaccharides, proteins and proteinaceous materials, oligonucleotides, RNA, DNA, cellulose, cellulose acetate, polyamides, polyimides and polyacrylamides. Gelatin is a standard matrix material for supporting photosensitive species, such as silver halide grains. Gelatin can also be cross-linked by chromium III ions, between carboxyl groups on gel strands.

The sensor may be prepared according to the methods disclosed in WO-A-95/26499, WO-A-99/63408 and WO-A-03/087789. The contents of these specifications are incorporated herein by reference.

The hologram in the sensor of the invention can be generated by the diffraction of light. The hologram may only be visible under magnification, or may be viewable under white light, UV light or infra-red radiation, under specific temperature, magnetism or pressure conditions, under light focussed in a specific fashion or under a laser having a specific frequency or wavelength. The holographic image is preferably of an object or gives a 2- or 3-dimensional effect.

The sensor may further comprise means for producing an interference effect when illuminated with laser light, preferably wherein the means comprises a depolarising layer.

The sensor may have a layer of a material covering all or a part of it which modifies a property of the light passing through it or acts as a filter. The material may be transparent and have a particular refractive index or may be act as a colour filter. Such materials are beneficial and are used to ensure that the analysis of any particular holographic response can be carried out easily and without ambiguity.

The invention also relates to a method of detection of an analyte in a sample, which comprises contacting the sample with the medium of a sensor according to the invention, and detecting any change of the optical characteristic. The analyte is preferably a chemical, biochemical or biological species. The change in optical characteristics can be detected by the naked eye or by using a device. A device can be also used to store, transmit or process data relating to the optical change. The device is preferably selected from the group consisting of an optical reader, a mobile phone, a computer and a digital camera. It is envisaged that any type of computer can be used, such as a laptop, a desktop, or a hand held device such as a personal digital assistant (PDA) which is a personal organizer device.

An article comprising a sensor according to the invention can be used in various fields. Such an article may be a transaction card, banknote, passport, identification card, smart card, driving license, share certificate, bond, cheque, cheque card, tax banderole, gift voucher, postage stamp, rail or air ticket, telephone card, lottery card, event ticket, credit or debit card, business card, or an item used in consumer, brand or product protection for the purpose of distinguishing genuine products from counterfeit products or identifying stolen products.

Alternatively the article may be an item of intelligent packaging. "Intelligent packaging" refers to a system that comprises part of, or an attachment to, a container, wrapper or enclosure, to monitor, indicate or test product information or quality or environmental conditions that will affect product quality, shelf life or safety and typical applications, such as indicators showing time-temperature, freshness, moisture, alcohol, gas, physical damage and the like.

The invention can be used with an article which is an industrial or handicraft item comprising a decorative element, selected from items of jewelry, items of clothing (including footwear), fabric, furniture, toys, gifts, household items (including crockery and glassware), architecture (including glass, tile, paint, metals, bricks, ceramics, wood, plastics and other internal and external installations), art (including pictures, sculpture, pottery and light installations), stationery (including greetings cards, letterheads and promotional material) and sporting goods, or an article which is a product or device for use in agricultural studies, environmental studies, human or veterinary prognostics, theranostics, diagnostics, therapy or chemical analysis, especially which is a test strip, chip, cartridge, swab, tube, pipette, contact lens, sub-conjuctival implant, sub-dermal implant, breathalyser, catheter or a fluid sampling or analysis device.

The sensor of the invention can be included on a transferable holographic film. The film is preferably present on a hot stamping tape. The security of an article can be enhanced by transferring onto the article the sensor from the film.

The invention also relates to a product comprising a sensor of the invention which is capable of generating data from said sensor and to a system which uses data generated by such a product for data storage, control, transmission, reporting and/or modeling.

The following Examples illustrate the invention.

Example 1

A support medium was formed by copolymerising 12 mol % 3-aminophenylboronic acid, 86.5 mol % acrylamide, and 1.5 mol % BAP as a cross-linker. A similar medium was then formed, using 1.5 mol % MBA as the cross-linker. Silver halide was then immobilised within each medium and a hologram recorded, using 2 pulses of laser light. Another medium was formed by the "silverless double polymerisation" of 12 mol % 3-aminophenylboronic acid and acrylamide, using 1.5 mol % MBA as the cross-linker. Again, a hologram was recorded in the medium.

The hologram of the sensor of the invention was considerably (of the order of 10-100 times) brighter than that the conventional sensors, even though only 2 pulses of laser light were used in its construction. Indeed, the hologram of the invention was so bright that it could even be viewed under a strip light. The responses of the various sensors were also compared, and were shown to be virtually identical. The diffraction peak of the sensor of the invention was highly monochromatic relative to those of the other two.

Example 2

A support medium was formed by copolymerising 5 mol % acrylic acid, 90 mol % of a 2:1 ratio of acrylamide:methacrylamide, and 5 mol % BAP as a cross-linker. Silver halide was then immobilised within the medium and a hologram was recorded. The sensor exhibited similar characteristics to the sensor of Example 1.

The invention claimed is:

1. A sensor comprising a medium and, disposed therein, a hologram,
   wherein an optical characteristic of the medium changes as a result of a variation in a physical property of the medium,
   wherein the fringes of the hologram are formed by silver grains, wherein the medium comprises a material which inhibits the binding of silver, wherein the variation of a physical property of the medium occurs in the presence of glucose or lactic acid, thereby defining the sensor as responsive to such an analyte, wherein the medium is a cross-linked material, and wherein the material of the medium is cross-linked with a bis(tertiary amide).

2. The sensor according to claim 1, wherein the hologram is generated by the diffraction of light.

3. The sensor according to claim 1, wherein the hologram is only visible under magnification or under laser light illumination.

4. The sensor according to claim 1, wherein the holographic image is of an object or gives a 2- or 3-dimensional effect.

5. The sensor according to claim 1, further comprising means for producing an interference effect when illuminated with laser light.

6. The sensor according to claim 5, wherein the means comprises a depolarising layer.

7. The sensor according to claim 1, wherein the hologram is viewable under white light, UV light or infra-red radiation.

8. The sensor according to claim 1, wherein the hologram is viewable under specific temperature, magnetism or pressure conditions.

9. The sensor according to claim 1, wherein the sensor has a layer of a material covering all or a part of it where the material is transparent or acts as a colour filter.

10. An article comprising the sensor according to claim 1, wherein the article is a transaction card; banknote; passport; identification card; smart card; driving license; share certificate; bond; cheque; cheque card; tax banderole; gift voucher; postage stamp; rail or air ticket; telephone card; lottery card; event ticket; credit or debit card; business card; or an item used in consumer, brand or product protection for the purpose of distinguishing genuine products from counterfeit products or identifying stolen products.

11. An article comprising the sensor according to claim 1, wherein the article is an item of intelligent packaging.

12. An article comprising the sensor according to claim 1, wherein the article is an industrial or handicraft item comprising a decorative element, selected from items of jewelry, items of clothing, fabric, furniture, toys, gifts, household items, architecture, art, stationery and sporting goods.

13. An article comprising the sensor according to claim 1, wherein the article is a product or device for use in agricultural studies, environmental studies, human or veterinary prognostics, theranostics, diagnostics, therapy or chemical analysis.

14. An article comprising the sensor according to claim 1, wherein the article is a test strip, chip, cartridge, swab, tube, pipette, contact lens, sub-conjunctival implant, sub-dermal implant, breathalyser, catheter or a fluid sampling or analysis device.

15. A method of detection of an analyte in a sample, which comprises contacting the sample with the medium of a sensor comprising a medium and disposed therein, a hologram, wherein an optical characteristic of the medium changes as a result of a variation in a physical property of the medium, wherein the fringes of the hologram are formed by silver grains, wherein the medium comprises a material which inhibits the binding of silver, wherein said method further comprises detecting any change of the optical characteristic, wherein the variation of a physical property of the medium occurs in the presence of glucose or lactic acid, thereby defining the sensor as responsive to such an analyte, wherein the medium is a cross-linked material, and wherein the material of the medium is cross-linked with a bis(tertiary amide).

16. The method according to claim 15, wherein the analyte is a chemical, biochemical or biological species.

17. The method according to claim 15 wherein any change in optical characteristic is detected or data relating to the optical change is stored, transmitted or processed using a device selected from the group consisting of an optical reader, a mobile phone, a computer and a digital camera.

18. A transferable holographic film comprising a sensor wherein the sensor comprises a medium and, disposed therein, a hologram, wherein an optical characteristic of the medium changes as a result of a variation in a physical property of the medium, wherein the fringes of the hologram are formed by silver grains, wherein the medium comprises a material which inhibits the binding of silver, wherein the variation of a physical property of the medium occurs in the presence of glucose or lactic acid, thereby defining the sensor as responsive to such an analyte, wherein the medium is a cross-linked material, wherein the material of the medium is cross-linked with a bis(tertiary amide), and wherein the film is present on a hot stamping tape.

19. A sensor comprising a medium and, disposed therein, a hologram, wherein an optical characteristic of the medium changes as a result of a variation in a physical property of the medium, wherein the fringes of the hologram are formed by silver grains, wherein the medium comprises a material which inhibits the binding of silver, wherein the variation of a physical property of the medium occurs in the presence of glucose or lactic acid, thereby defining the sensor as responsive to such an analyte, wherein the medium is a cross-linked material, wherein the material is obtainable by the polymerization of monomers including acrylamide-based monomers, wherein the monomers include acrylamide and/or methacrylamide, and wherein the material of the medium is cross-linked with 1,4-bis(acryloyl)piperazine.

* * * * *